United States Patent [19]

Corella

[11] Patent Number: 4,693,365

[45] Date of Patent: * Sep. 15, 1987

[54] PACKAGE, INSTRUMENTATION, SYSTEM AND METHOD FOR PACKAGING FLACCID ITEMS, FILAMENTS AND THE LIKE

[76] Inventor: Arthur P. Corella, 8166 Vanscoy Ave., North Hollywood, Calif. 91602

[ * ] Notice: The portion of the term of this patent subsequent to Apr. 1, 2003 has been disclaimed.

[21] Appl. No.: 844,199

[22] Filed: Mar. 26, 1986

Related U.S. Application Data

[63] Continuation-in-part of Ser. No. 723,353, Apr. 15, 1985, Pat. No. 4,579,221.

[51] Int. Cl.$^4$ .............................................. A61L 17/02
[52] U.S. Cl. ................... 206/63.3; 206/63.5; 206/388; 206/390; 53/412
[58] Field of Search ....................... 206/409, 390, 63.3, 206/63.5, 484, 388; 53/412, 546

[56] References Cited

U.S. PATENT DOCUMENTS

| | | | |
|---|---|---|---|
| D. 173,640 | 12/1954 | Cargill et al. | 53/412 X |
| 2,921,676 | 1/1960 | Carignan | 206/409 |
| 3,210,908 | 10/1965 | Samberg | 53/546 |
| 3,636,678 | 1/1972 | Maros et al. | 53/412 |
| 3,795,080 | 3/1974 | Smolderen et al. | 53/412 |
| 3,807,118 | 4/1974 | Pike | 53/412 X |
| 4,063,398 | 12/1977 | Huffman | 53/412 |
| 4,168,000 | 9/1979 | MacRitchie | 206/63.3 |
| 4,579,221 | 4/1986 | Corella | 206/63.3 |

Primary Examiner—Horace M. Culver
Attorney, Agent, or Firm—Donald Diamond

[57] ABSTRACT

A package (20, 40, 48, 56, 72) is sealed to enclose dental floss or other filament (22). The filament is sealed at its end portions (22b) within sealed ends (26b, 26d; 46b, 46d; 50b, 50d; 62b, 62d; 74b, 74d) of the package, and a bunched-up filament portion is sealed within the package. A notch (30) with a cut (30a and 30b), a tear line 54, a tear-away tab (64) or simply the package material which is easily tearable, enables the package to be opened, by using a greater or lesser sized segment (e.g., 34; 64; 72a or 72b) of the package as a handle to draw the filament untangled and unknotted from the package. The package is formed using instrumentation including a feed tube (114) and a mandrel (116) which are concentrically positioned and relatively movable with respect to one another in timed movements. These movements are coordinated with movements of accompanying sealers (74, 98), holders (78, 102) and a cutter (104), to draw an uncut length of filament (22) between two films (72a, 72b) of wrapping material, and bunch up a measured amount (22a) of the filament for deposit into an open-ended compartment (28) formed from the wrapping material.

23 Claims, 17 Drawing Figures

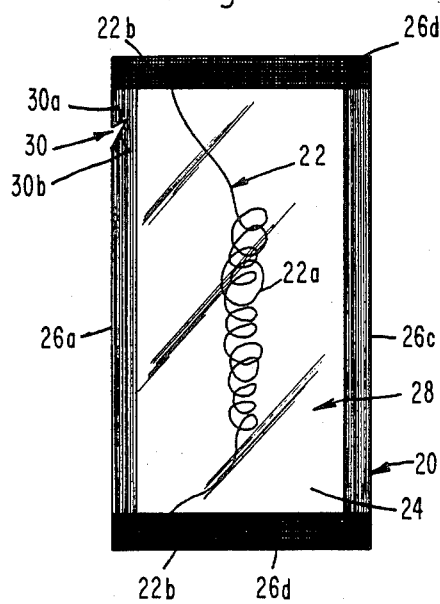
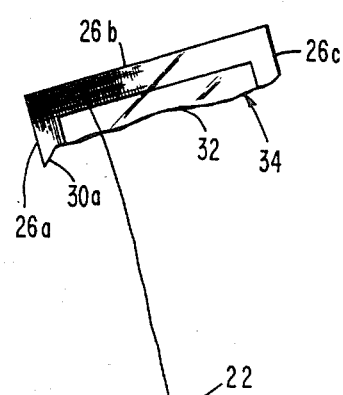
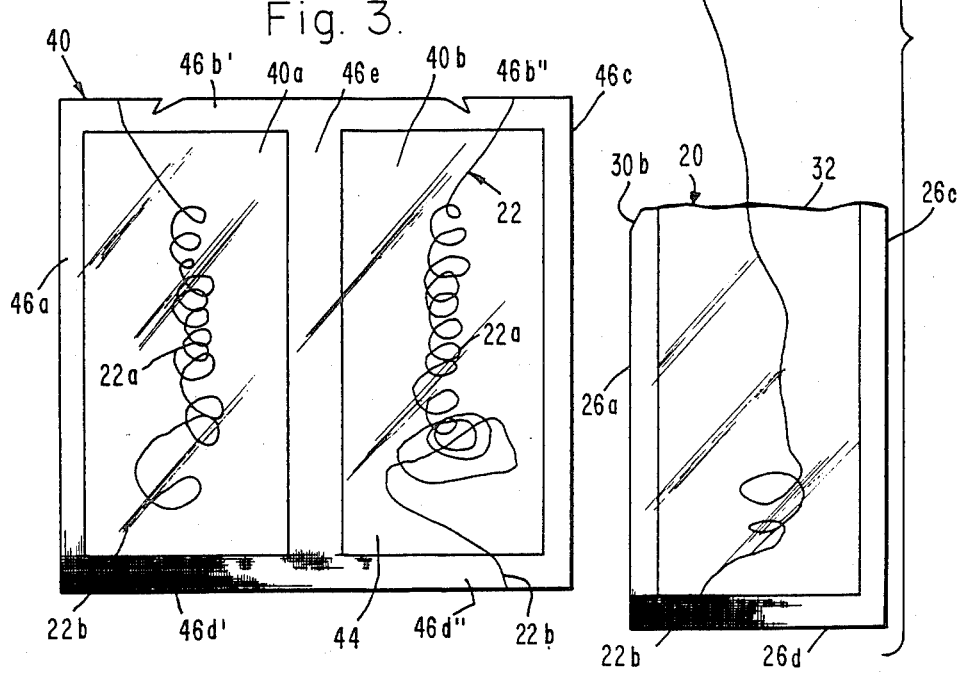

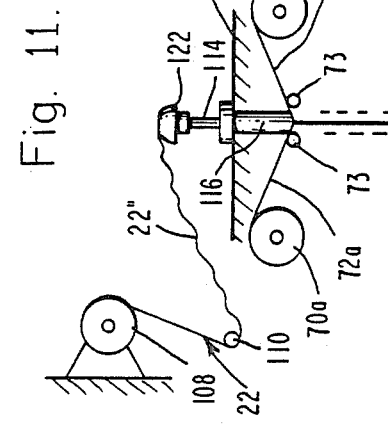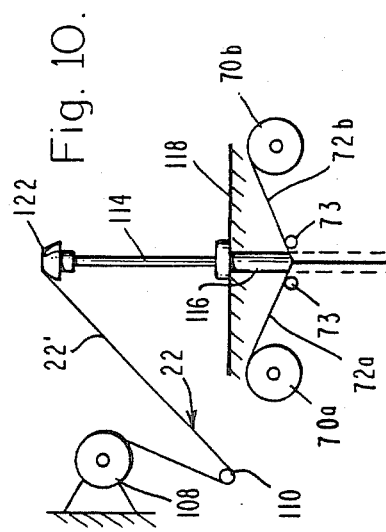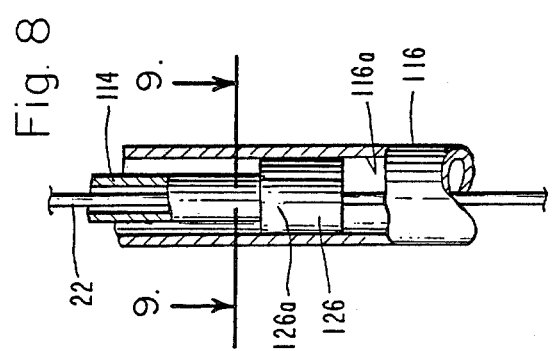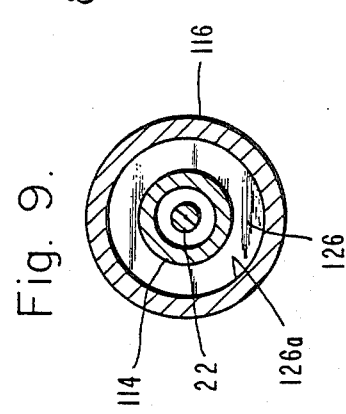

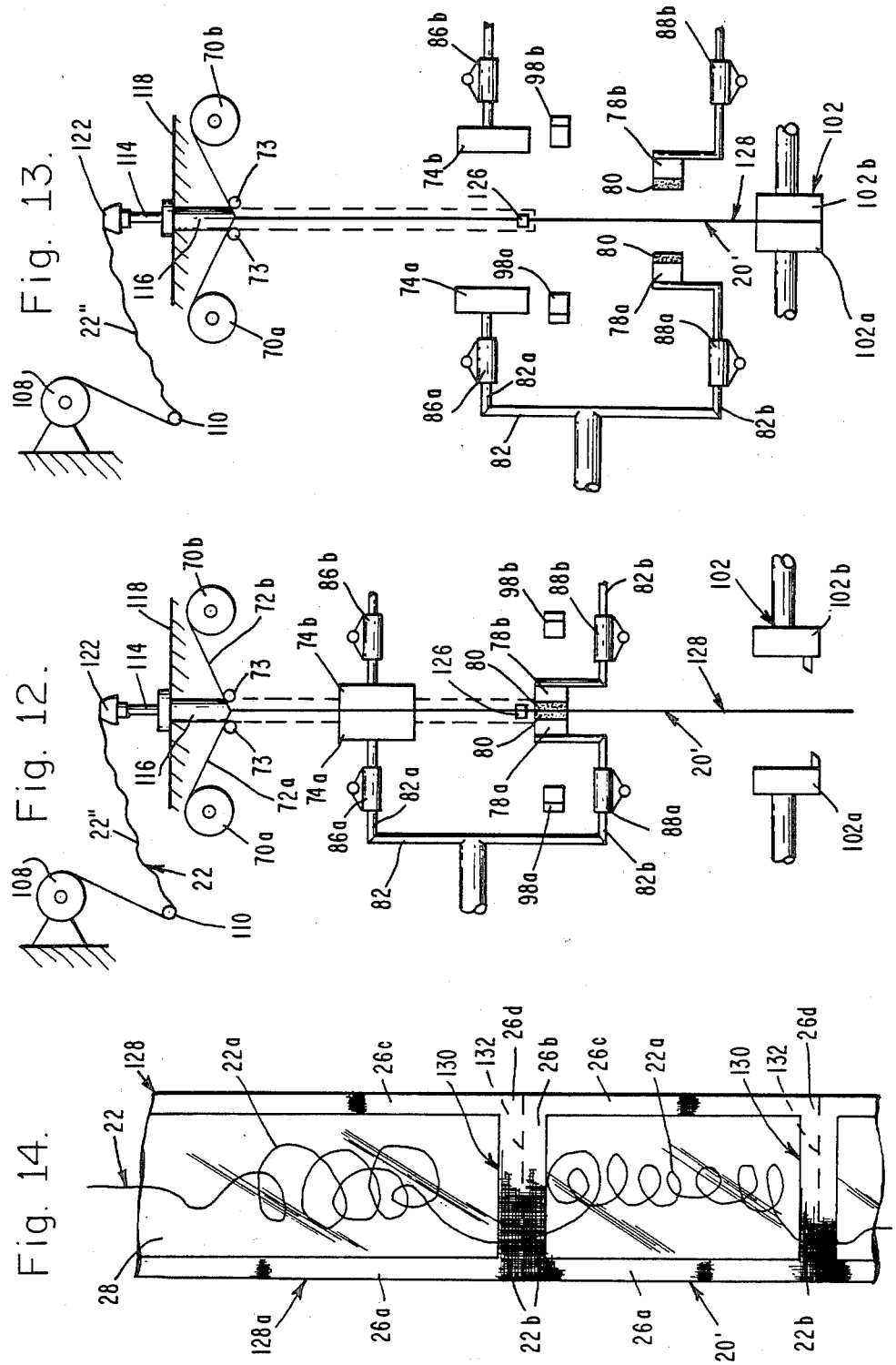

PACKAGE, INSTRUMENTATION, SYSTEM AND METHOD FOR PACKAGING FLACCID ITEMS, FILAMENTS AND THE LIKE

This is a continuation-in-part of copending application, Ser. No. 723,353 filed Apr. 15, 1985 and now U.S. Pat. No. 4,579,221.

The present invention relates to a package, instrumentation, system and method in which flaccid items, filaments and the like are packaged from uncut supplies of the same, and from which the flaccid items can be packaged and withdrawn in an untangled and an unknotted condition.

Packaging of tablets, granular and liquid materials, and single relatively rigid items in sealed packages is a well-developed art. Because of their weight and substance, they are easily inserted or gravity dropped into the package enclosure. Such an enclosure may be fabricated from a continuous tube or a pair of sheets respectively sealed where the bottom or bottom and sides of the enclosure is to be formed and, for multiple package formation and filling, also intermediate the sides. The construction and use of equipment, and processing associated therewith, employed for such packaging are well known.

Conventional equipment and its use, however, are not altogether satisfactory when the items to be packaged are flaccid, such as filaments, wires, dental floss, and the like. In particular, conventional equipment presently is not automated at least for efficient packaging of such flaccid items. Accordingly, present practice is to stuff them into the enclosures to be formed into the packages. Whether or not efficiently performed, such practice militates against automation, and increases the number of rejects. Packaging costs, therefore, correspondingly increase.

A known package, which contains a flaccid item, specifically a thread, is one which encloses the thread with a bandage, e.g., a BAND-AIDS ® package; however, the thread therein is used solely to open the package, and is not the primary item intended to be packaged. In addition, because the thread is flaccid and not capable of self-support, it is necessary to adhere or otherwise secure the thread to one of the sides of the package, to provide the necessary support during manufacture of the package and its contained bandage.

Furthermore, opening of any package and removal and extraction of the filament or thread should be easy, without entanglement or knotting of the filament and without slippage of the thread from the package, as sometimes occurs in the BAND-AIDS ® package. Also, instructions, if such are needed or desired, for opening the package should be as simple as possible, so as to minimize any potential error, regardless of the user, so that the filament can be correctly extracted, strictly in accordance with the practice of the present invention.

SUMMARY OF THE INVENTION

The present invention avoids and overcomes these and other problems, and facilitates proper opening of the package. Individual packages, which contain one or more flaccid items, depending on the customer's requirements, are sealed within an envelope. End portions of the flaccid item extend into and are sealingly entrapped within the seals. The construction of a package will suggest its method of opening. For packages whose material is easily tearable, it is necessary only to indicate where the user is to tear the package, such as by a physical tear line or other graphic representation and, if desired, accompanied with the imprinted message "tear here," to direct the user's attention as to the proper technique for opening the package. The tear line may be imprinted on both sides of the package to avoid any possible user error. A tab with an end of each filament may also be extended from the package to facilitate tearing into and opening of the package and for extracting the filament therefrom. Where the material of the package resists tearing, a cut is extended partially into the seal, preferably with an imprinted tear line and message as previously indicated, and is positioned to enable separation of an end of the flaccid item, along with a segment of the package seal in which it is entrapped, from the remainder of the package so that the segment acts as a handle by which the flaccid item may be withdrawn from the package in an untangled and an unknotted manner. An equivalent cut for starting the tear is the sharp angle where the above-mentioned tab meets the package. In some packaging arrangements, it is not necessary to provide any preformed cuts or instructions for opening the package; thus, no printing or cuts are used.

In a preferred embodiment, the packaging for enclosing a flaccid item comprises a fully sealed enclosure (i.e., a package) having a compartment and a sealed entry to the compartment. Continuous central and end portions of the flaccid item are respectively housed within the compartment and extend into and are sealed within the sealed entry near one or more corners of the package. A tear line and message for package materials which can be easily torn, or a notch adjacent one of the item's end portions for package materials which resist tearing, enables the seal to be torn in a controlled manner to remove the package's corner and the flaccid item entrapped therein so that the package is not only opened, but access is also provided to withdraw the flaccid item from the compartment. The corner thus operates as a handle for drawing the flaccid item evenly, and without entanglement and knotting, through the opening. It is understood, of course, that tearing through the center of the package provides an even larger handle than a corner. The packages are formed in a continuous manner from uncut lengths of the flaccid item and of the material to be formed into the package. The packaging material is taken from tubular stock formed generally as a sheath or from a pair of appropriately sealed sheets to provide a compartment with a sealed bottom and contiguous walls terminating at an open top. The flaccid item is positively fed or deposited into the compartment in an untangled manner by a feeding mechanism, rather than by gravity. The compartment is then sealed at its open end and cut into into individual packages.

The preferred feeding mechanism, when the flaccid item comprises a filament, includes a feed tube concentrically placed and slidable within a tubular mandrel. The feed tube is moved in sequential operations relative to the mandrel and with respect to compartment holding and sealing devices so that the packages are appropriately formed.

Several advantages are obtained therefrom. The flaccid item is deposited into, contained in, and removed from the package in an untangled and unknotted condition. A segment of the package is used as a handle in the removal. The packaging process is automated to eliminate unnecessary and otherwise relatively slow handling procedures. Thus, manufacturing costs are reduced. In conjunction therewith, the use of existing equipment is facilitated, to avoid the purchase of additional and possibly specially designed manufacturing equipment. Standard packaging materials can be used, so that new techniques for their handling and bonding or sealing are also avoided. As a consequence, advertising and/or labelling information may be incorporated, as is conventional with standard packaging.

Other aims and advantages, as well as a more complete understanding of the present invention, will appear from the following explanation of exemplary embodiments and the accompanying drawings thereof.

BRIEF DESCRIPTION OF THE DRAWINGS

FIG. 1 illustrates a package configuration formed in accordance with a first embodiment of the present invention, in which a single length of flaccid item is sealed within an enclosure;

FIG. 2 is illustrative of the opening of the package depicted in FIG. 1, and the drawing of the flaccid item therefrom in an untangled and unknotted manner with the aid of a segment of the package operating as a handle;

FIG. 3 shows another package configuration formed in accordance with a second embodiment of the present invention, in which a pair of flaccid items are sealed within separate enclosures within a single package;

FIGS. 8 and 9 are cross-sectional views of the feed tube and the mandrel of the mechanism, apparatus or instrumentation of FIG. 7, used to insert the filament into a package envelope;

FIGS. 10–13 are simplified diagrammatic views of the instrumentation shown in FIGS. 7–9 and the steps showing its use for forming such packages depicted in FIGS. 1 and 4, with FIGS. 12a and 12b being enlargements of portions of the instrumentation and in-process packages respectively in FIG. 12 and preceeding FIG. 13, detailing important aspects thereof; and FIG. 14 is a side view of a portion of a package in process of formation, comprising an open-ended sheath and a completed package attached thereto prior to its separation from the sheath.

DESCRIPTION OF THE PREFERRED EMBODIMENTS

Figure 4:
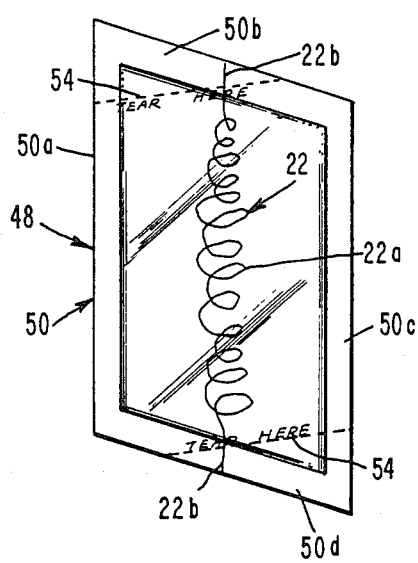
FIGS. 4–6 illustrate still further package configurations of other embodiments of the present invention, with FIG. 4 being representative of both front and back views of one embodiment, with FIG. 5 illustrating the tearing and opening of the package in which a torn tab portion thereof is used as a handle to draw the flaccid item out in an untangled and unknotted manner and with FIGS. 6a and 6b depicting a plain package in its sealed and center-opening tear which does not require a preformed cut or other imprinted instruction for opening the package.

Accordingly, FIG. 1 illustrates a package or sealed enclosure 20, which contains a single continuously extending, uncut flaccid items 22. By flaccid, it is meant that item 22 has little or no rigidity or firmness and, therefore, is incapable of self-support; thus, when unsupported, it may be limp.

Flaccid item 22 comprises a central portion 22a and end or terminal portions 22b. Central portion 22a is bunched-up in an untangled manner, that is, it is or may be massed together, but still be capable of being readily separated, so as to be free from being or becoming knotted. Such an untangled condition, as will be more fully explained below, permits the flaccid item to be extracted in an unknotted and untangled manner from its enclosure.

Representative flaccid items include filaments, for example, of thread or ribbon style dental floss, or of natural fiber, synthetic fiber, metallic wire, or of flat material with or without printing thereon, e.g., a paper with a message thereon, and combinations thereof. In addition, if desired, non-flaccid devices, such as a needle, may be packaged with the flaccid item within the package.

A typical package has a rectangularly-shaped flat configuration defined by a pair of large-surfaced, flat walls 24 which are sealed together at their perimeters as indicated by indicia 26a–26d to form a compartment 28 in which the flaccid item is contained.

As a further example of packaging techniques, package 20 may comprise a transparent wrapping to permit filament 22 to be seen or, at a minimum, translucent wrapping to permit display of a message.

The wrapping comprises any conventional, suitable material, composition or laminate, e.g., paper, plastic (such as polyethylene and MYLAR ® polyester film), aluminum foil, polyester-polyethylene, polyethylene-paper, and polyethylene-metal foil. In a laminate, the polyethylene forms the inner face and the paper or foil form the outer face of the walls. Polyethylene is preferred because it is readily heat-sealable to form the sealed peripheral walls. Paper or metal foil enables a message, illustration, and the like to be printed thereon.

As stated above, the wrapping for package 20 is shown as having seal 26a–26d extending fully around its periphery, in which seals 26a and 26c may be termed side seals and seals 26b and 26d may be termed top and bottom seals, respectively.

If package 20 were formed from tubular stock, it would have a single side seal at most and, therefore, be closed only with top and bottom seals, like seals 26b and 26d of FIG. 1, to form a sealed enclosure. These differences in the construction of the seals result both from the stock selected for the particular wrapping and from the machinery used in forming the wrappings into the packages. The wrapping for package 20 is taken from a pair of sheets, sealed together, for example, by use of the sealing die illustrated in FIG. 7.

Furthermore, it is not necessary that both end portions 22b of filament 22 extend into separate seals, such as top and bottom seals 26b and 26d of package 20; rather, any package may be so manufactured that the end portions extend through the same seal at the top or bottom of the package. Also, the filament end portions may terminate at the very edge of the package, or extend therebeyond.

An important feature of the present invention is a design which permits easy opening or rupture of any package and withdrawal of the filament in an untangled and unknotted manner from its sealed compartment. To this end, the filament is deposited into the package in an untangled and unknotted manner, i.e., in a bunched-up, readily separable mass, as will be described below.

Depending upon the construction of the package, the means by which it is opened will vary, of which the following techniques are illustrative. For a construction in which the material is relatively difficult to tear, a curved, chevron or V-shaped notch 30 for the filament is partially cut into at or adjacent to at least one of the seals at a filament end, but does not extend completely therethrough.

As shown, notch 30 is cut into side seal 26a of package 20 of FIG. 1. The notch is so placed that the filament to be extracted from its package is positioned between the notch and the adjacent edge of the package, e.g., that edge which encompasses top seal 26b of package 20 of FIG. 1.

It is preferred that the notch be configured to encourage a directed tearing of the package across the filament. Thus, as an aid to the person opening the package, the notch may be defined by a first cut 30a and a second cut 30b both of which can be pointed in the direction in which the package is to be torn. However, this directing is not required; the notch only is a beginning point for tearing the package open.

Such directional tearing is shown in FIG. 2, in which the tear in package 20 is denoted by indicium 32 and extends parallel to top seal 26b from side 26a to side 26c to form an end segment 34. If desired, the tear may extend diagonally from side 26a to top 26b to form a corner segment. In either case, the segment, e.g., end segment 34, entraps a filament end portion 22b, so that the package segment operates as a handle by which bunched-up portion 22a of the filament can be withdrawn easily and in an untangled and unknotted manner from the package.

A double package 40, similar to package 20 of FIG. 1, is shown in FIG. 3. In this embodiment, package 40 comprises a pair of sealed enclosures 40a and 40b, each containing a flaccid item 22 formed like the flaccid item of FIG. 1. Package 40 comprises a pair of flat walls 44 which are peripherally sealed to form a side seal 46a, a pair of top seals 46b' and 46b", a second side seal 46c, a pair of bottom seals 46d' and 46d", and an additional separating seal 46e intermediate side seals 46a and 46c.

Separating seal 46e is characterized as preferably encompassing an enlarged, continuously sealed area which may be centrally perforated to enable easy separation of enclosure 40a from enclosure 40b. Thus, individual sterility can be provided between the two enclosures and enables one to be opened without affecting the other; however, such a perforated seal area may be dispensed with if separation is not desired.

Figure 6A:
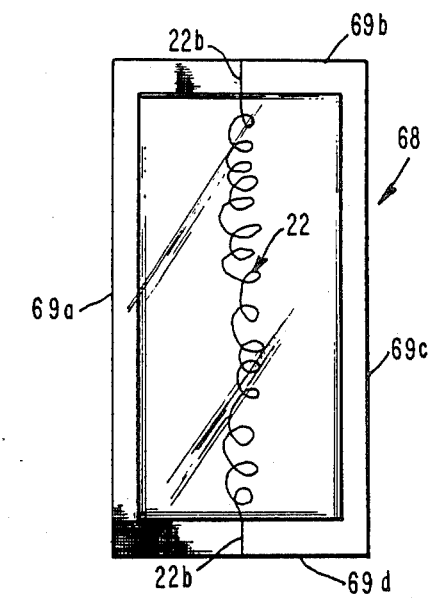
Figure 5:
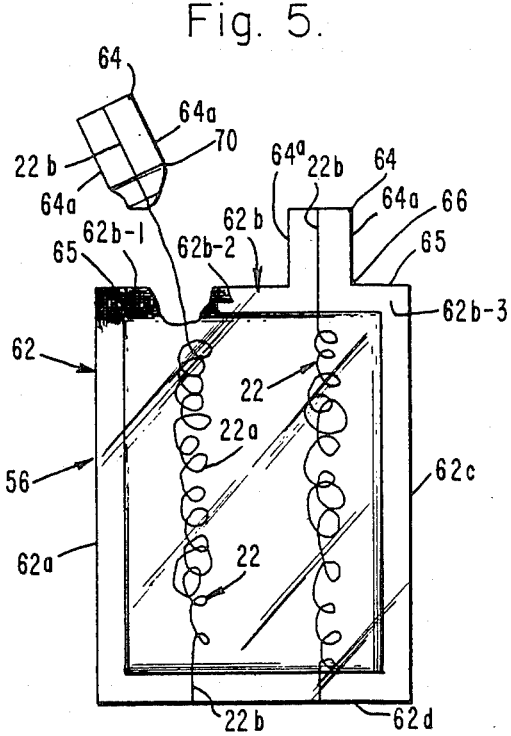
Figure 6B:
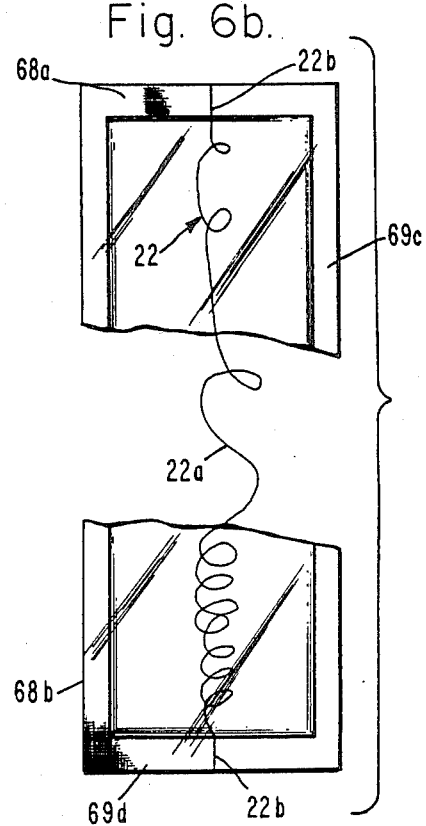

For packages having a construction whose material is readily tearable, notch 30 is not required although, if desired, it may be retained. FIGS. 4-6 illustrate this concept. While the embodiments of FIG. 4, FIG. 5 and FIGS. 6a and 6b depict single and double filament packages, it is obvious that double filaments may be placed in the single filament package, and vice-versa.

In FIG. 4, a package 48 is shaped as a parallelepiped having a sealed periphery 50 which includes sealed edges 50a–50d comprising top and bottom edges 50b and 50d and side edges 50a and 50c, in which the intersection between edges 50a and 50b and between edges 50c and 50d form acute angles. Filament 22 extends between top and bottom edges 50b and 50d and its bunched-up central portion 22a terminates at ends 22b. Ends 22b are sealed within the top and bottom sealed edges in the same manner as before. This construction employs a pair of dashed tear lines 54 and instructions "TEAR HERE" on both sides of package 48 extend across the acute angle portions of the package and permit the user to open the package at either end. If desired, only a single tear may be extended across the package and also, if desired, it may be placed centrally between the top and bottom edges (see also FIGS. 6a–6b).

The embodiment depicted in FIG. 5 comprises a package 56 enclosing a pair of filaments 22. As in the prior embodiments, package 56 has a sealed periphery 62, including sealed top and bottom edges 62b and 62d and sealed side edges 62a and 62c. Filament ends 22b of each pair are sealed within the top and bottom edges. For this construction, a pair of tabs 64 are integrally formed in and extend from sealed top portion 62b and thereby divide it into three portions 62b-1, 62b-2 and 62b-3 and respectively enclose both pairs of filament ends 22b. The tabs have sides 64a which intersect top edge portions 62b-1, 62b-2 and 62b-3 to form apices 66. These apices act in the same manner as that of notch 30 of FIGS. 1 and 2, i.e., they permit the package to be torn in a controlled manner so that the removed tab, as shown, will become the handle for extracting the filament in an untangled fashion from package 56.

When the package, its use and its material are such that neither a cut in nor imprinting on the package are necessary or desirable, the embodiment depicted in FIGS. 6a–6b may be employed. Here, a package 68 enclosing dental floss 22 is sealed at its peripheral edges 69a–69d, similar to that described previously. To illustate the simplicity of the present invention, according to this construction, package 68 is torn generally through its center from side 69a to side 69c, so that each approximate half 68a and 68b of the package acts as a handle enclosing floss ends 22b and permits bunched-up portion 22a to be extracted in an untangled manner.

Figure 7:
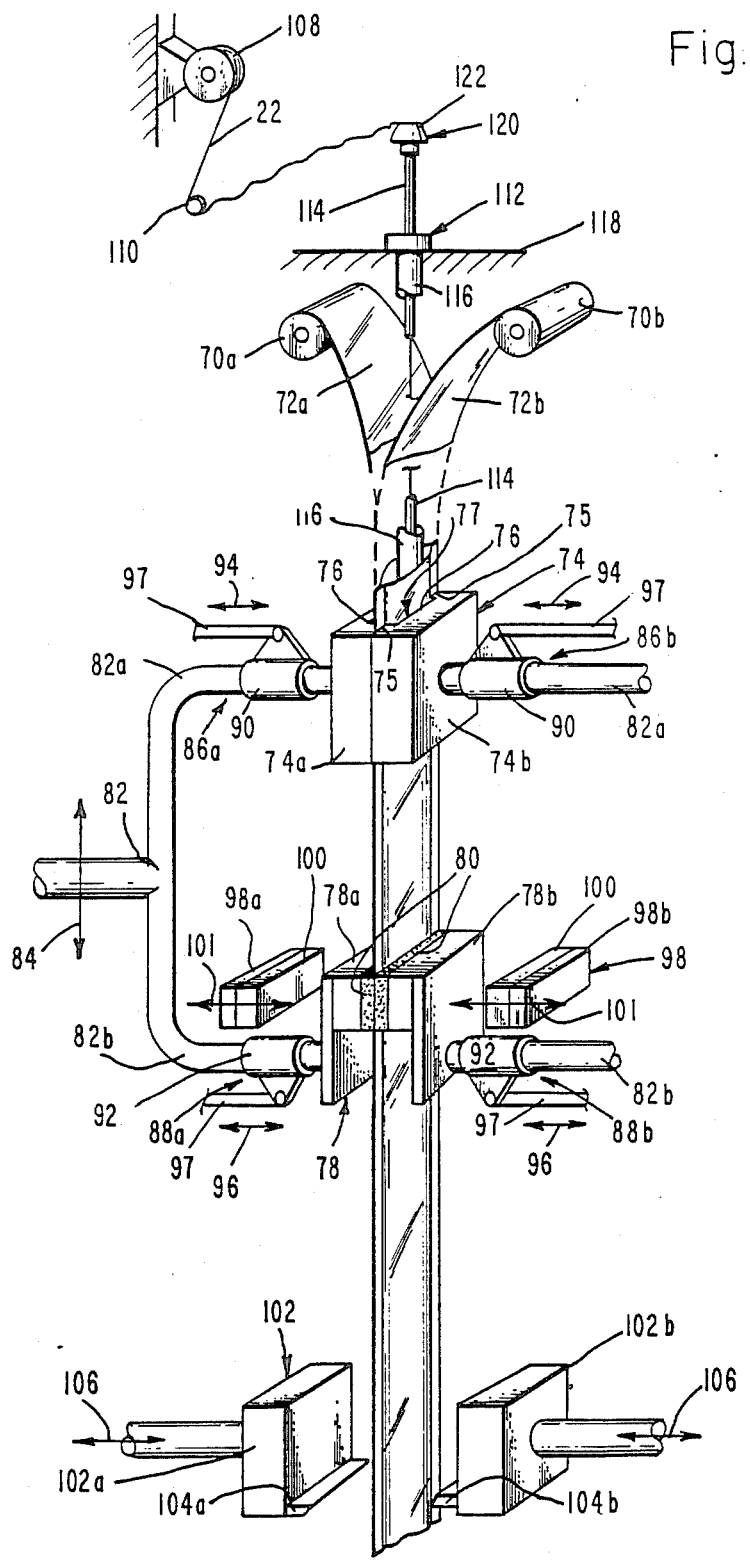
FIG. 7 depicts a mechanism, apparatus or instrumentation for forming a package, such as shown in FIGS. 1 and 4.

Packages 20, 40, 48, 56 and 68 may be manufactured by the mechanism illustrated in FIG. 7 and the process steps associated therewith as illustrated in FIGS. 10-13. The arrangement uses basically standard packaging machinery, which is modified with the addition of novel filament feeding devices and relative movements among the several mechanical elements.

The packaging instrumentation includes two rolls or sources 70a and 70b of two films of wrapping material 72a and 72b, each of which may comprise either a single layer of polyethylene or a laminate of an inner layer of polyethylene and an outer layer of any suitable material, such as of paper or aluminum or any other materials or combinations as previously suggested. Polyethylene is preferred because it is easily heat-sealable and forms a secure and sanitary package. The outer layer is selected for decorative, message bearing and related or other reasons.

Films of wrapping material 72a and 72b are guided over rollers 73 (see also FIGS. 10-13) for enabling them to be fed within a sealing mechanism 74 comprising mating halves 74a and 74b. Each half includes a pair of vertical, parallelly extending contactable faces 75 separated by a vertical channel 76. The mating channels form a vertically extending tubular recess 77, shown in a generally rectangular configuration, although other geometric shapes are acceptable, provided that a through opening results. Contactable faces 75 of the mating halves may have interfitting ridges and grooves so that, when sealing mechanism 74 is heated and wrapping material films 72a and 72b are pressed between the vertically extending faces, the entrapped inner layer from the two films of wrapping material are sealed together at their edges but not at their centers, as permitted by recess 77 to form side seals, such as side seals 26a and 26c, 50a and 50c, 62a and 62c, and 69a and 69c, respectively of FIGS. 1, 4, 5 and 6a–6b.

Positioned below sealing mechanism 74 is a holder 78 comprising a pair of holder halves 78a and 78b, which include resilient pads 80 of elastomeric material. Each half of sealing mechanism 74 and of holder 78 is movable towards and away from one another respectively by paired, linearly moveable mechanisms 86a–86b and 88a–88b.

Sealing mechanism 74 and holder 78 are connected by a coupling 82 which moves respective sealing halves 74a and 74b and holder halves 78a and 78b up and down in unison, as represented by double-headed arrow line 84. Sealing mechanisms 74a and 74b and holder halves 78a and 78b are slidably mounted on respective arms 82a and 82b of coupling 82.

Mechanisms 86a–86b and 88a–88b include respective slidable sleeves 90 and 92 on arms 82a and 82b which couple both halves 74a–74b and 78a–78b to arms 82a and 82b to permit horizontally rectilinear movement of sealing mechanism 74 and holder 78 with respect to one another and to coupling 82, as denoted by indicia 94 and 96 and as will be further explained with respect to the operation of the machine shown in FIGS. 10–13. Mechanisms 86a–86b and 88a–88b may, for example, comprise a hydraulic piston having one end secured to coupling 82a and 82b and the other end to sealing mechanism 74 and holder 78 through links 97.

A second sealing mechanism 98 comprises sealing halves 98a and 98b which are disposed to move only towards and away from one another, as represented by double-headed arrow lines 101. Each half includes a horizontally disposed sealing surface 100 which, when heated and pressing films 82a and 82b together, simultaneously form top and bottom seals, such as seals 26b and 26d of FIG. 1, but of successive packages, as will be better understood with the description of the steps associated with FIGS. 10–13.

A holding and cutting mechanism 102 is positioned below horizontally sealing mechanism 98 and holder 78. The holding and cutting mechanism includes a pair of holder halves 102a and 102b and a pair 104 of knife edges 104a and 104b, respectively attached thereto. The holding and cutting mechanism halves are constrained to move towards and away from one another as represented by double-headed arrow lines 106. Thus, when the halves move towards one another to grip a section of completed packages still attached to other packages, some of which are still in process of completion, knife edges 102a and 102b separate the lowermost package from the remaining packages.

In the packages of FIGS. 1 and 3, flaccid item 22, which is illustrated in FIG. 7 et seq. as a filament such as of dental floss, is supplied from one or more spools or bobbins 108 as a continuous, uncut length, which is extended about a guiding roller 110 into a feeding mechanism 112. The feeding mechanism comprises a feed tube 114 and a tubular mandrel 116, which are concentric and relatively movable with respect to one another. Preferably, however, feed tube 114 is movable and mandrel 116 is fixed to a support 118. Recess 77 of sealing mechanism 74 is wider than mandrel 116 and, therefore, extends about and preferably is not in contact with the mandrel. A collar 122 is affixed to the upper end of feed tube 114 and is provided with an upper guiding surface having the general shape of a half doughnut, to provide a rounded annular entry for filament 22.

As best shown in FIGS. 8 and 9, feed tube 114 is terminated at its end by a piston 126. The piston is bonded, threaded or otherwise affixed to feed tube 114 so that they move together within mandrel 116. It is preferred that the end of the piston extend downwardly from the end of the tube and that a properly dimensioned small hole be provided in piston 126 through which filament 22 is threaded. The hole is smaller than the inside dimension of the tube and is so sized as to exert a frictional hold on the filament sufficient that it can be pushed by the piston into package compartment 28. This prevents the feed tube from exerting a detrimental drag on the filament. A peripheral surface 126a of the piston has essentially the same dimension and configuration as inner surface 116a of mandrel 116 to provide a close interfit between the surfaces. To minimize friction, piston 126 is formed from polytetrafluoroethylene or an equivalent composition, while feed tube 114 and mandrel 116 are preferably metallic, e.g. of stainless steel or the like.

The sequence of process steps is illustrated in FIGS. 10–13, with further reference to a strip of packages in formation being designated by indicium 128. Strip 128 is shown in diagrammatic edge view in FIGS. 10–13 and in full side view in FIG. 14. Thus, the FIGS. 10–13 view, in its simplified representation, does not illustrate the thickness of package strip 128 nor the bulging out of wrapping material 72a and 72b.

In FIG. 14 only a single completed entire package, identified by indicium 20', a portion of another completed package, and a partially completed package 128a are shown. The strip in FIGS. 10–13 may include a greater number than is illustrated in FIG. 14. Also, as FIG. 14 depicts, an enlarged sealed area 130 connects completed packages 20' to strip 128, because the completed packages have not yet been separated from strip 128. A dashed separation line 132 through an enlarged sealed area 130 is shown in the drawing, but is not used in reality, to represent where the separation is between sealed bottom 26d of one package from sealed top edge 26b of an adjacent package. It is because of the distinction made herein between separated and non-separated packages that the separated and non-separated packages are distinguished respectively by indicium 20 in FIG. 1 and indicium 20' in FIG. 14.

As shown in FIG. 10, one or more packages 20' have already been completed and separted by cutter blades 104 from the remainder of the packages in strip 128 in production, with holding and cutting mechanism pressing in contact with strip 128. Also, second sealing mechanism 98 and its horizontal sealing halves 98a and 98b are in contact with strip 128 to form sealed area 130 (see also FIG. 14). Piston 126 and feed tube 114 are at their uppermost position, having drawn in an amount of filament 22 sufficient, in preparation for a subsequent step, for depositing a bunched-up amount 22a of filament 22 into an open end within portion 128a of strip 128 and into compartment 28 upon the lowest travel of piston 126 at the lower end of feed tube 114. That amount of filament is positioned between piston 126 and second sealing mechanism 98. At this point, the filament is taut, as illustrated in FIG. 10 by indicium 22'.

Also, as shown in FIG. 10, vertical sealing halves 74a and 74b and holder halves 78a and 78b are in their lowermost positions and spaced back from package strip 128.

In the transition of movement of the instrumentation from FIG. 10 to FIG. 11, feed tube 114 and its piston 126 move downwardly and deposit an amount of the filament as bunched-up portion 22a into an already formed open compartment 28. As a result of feed tube movement, the tautness of the filament relaxes, as shown by indicium 22″. Also, at the same time of the transitional movement from FIG. 10 to FIG. 11, second sealer mechanism 98 is moved back from strip 128, followed by movement upward of sealing mechanism 74 and holder 78 to their uppermost positions shown in FIG. 11, in readiness (as described with respect to FIG. 12) to be moved towards one another, respectively, to form side seals 26a and 26c (FIG. 14) from web portions 72a and 72b and to press against the wrapping material and the bunched-up filament residing therein. Strip 128 is held in position by holding and cutting mechanism 102.

In the transition between FIGS. 11 and 12, heated sealer halves 74a and 74b and holder halves 78a and 78b are then respectively moved towards one another, as shown in FIG. 12, to seal the two films of the wrapping material together at their sides to form sealed sides 26a and 26c and open compartment 28. Just prior thereto, because holder 78 is slightly in advance of sealing mechanism 74, holder halves 78a and 78b grip the wrapping material and filament portion 22a therebetween. This differential horizontal movement is effected by coordinated respective movements of mechanisms 86a–86b and 88a–88b. Following the gripping by holder 78, holding and cutting mechanism 102 moves away from strip 128.

Figure 12A:
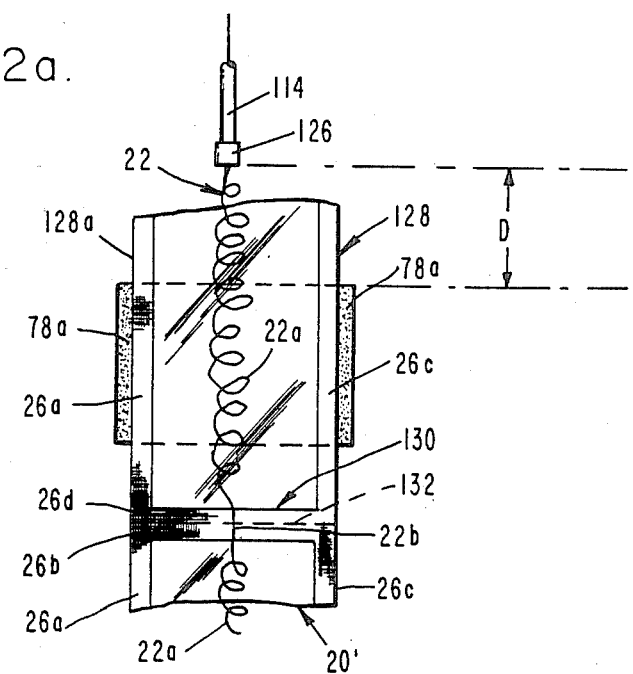
Figure 12B:
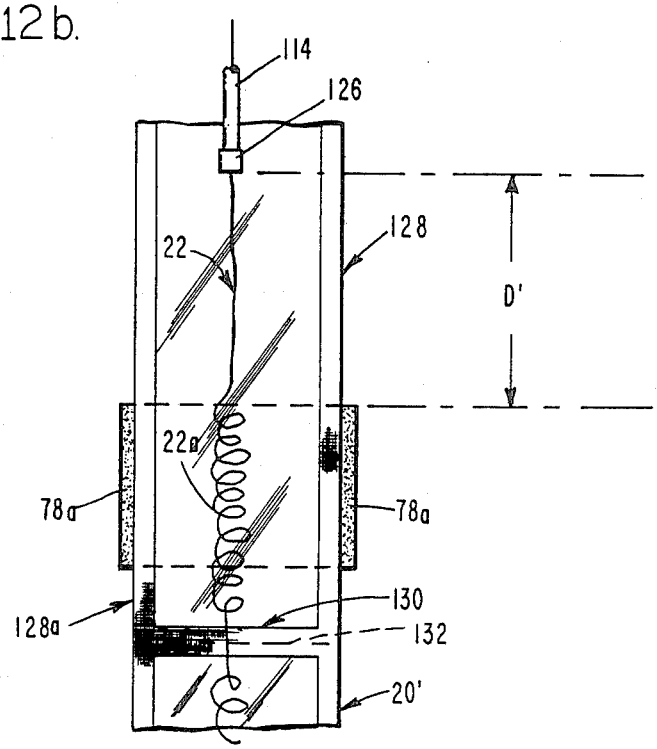

In the interval between the positions of the apparatus shown in FIGS. 12 and 13, as shown in FIGS. 12a and 12b, coupling 82 moves sealer 74, holder 78 and strip 128 held thereby downwardly. This downward movement is required to straighten the filament out prior to its being sealed by sealing halves 98a and 98b. Specifically, FIG. 12a is an enlarged view of a portion of the instrumentation illustrated in FIG. 12, where only holder half 78a is seen although, of course, it with other holder half 78b presses against opposite sides of strip 128. FIG. 12a also shows a freshly deposited bunched-up section of filament 22 which extends from sealed area 130 to piston 126 of feed tube 114 by a distance D. An intermediate portion of the larger extent of the freshly deposited bunched-up filament section is held between holder halves 78a and 78b. Before sealer halves 98a and 98b move against strip 128, it is desirable to straighten out that bunched-up portion extending between holder 78 and piston 126. This straightening out is effected by a slight downward movement of holder 78 with respect to piston 126, and is denoted by distance D′. For purposes of illustration, the movement between distances D and D′ from FIG. 12 to FIG. 13 and vice-versa from FIG. 13 to FIG. 10 is exaggerated to facilitate the viewing of the drawings.

After completion of the downward movement, as shown in FIG. 13, combined holder and cutting mechanism 102 move together both to grip strip 128 and to separate the lowermost completed package from the strip along separation line 132 (see FIG. 14). The sealer and holder halves 74a, 74b, and 78a, 78b are then moved outwardly from strip 128.

Thereafter, as illustrated in FIG. 10, heated horizontally sealing halves 98a and 98b are moved into contact with the strip to form sealed area 130 (see FIG. 14). During this time, piston 126 and feed tube 114 move up to their uppermost point to extend the measured length of filament 22 from the end of the feed tube and to make the filament taut at 22′. In the interval between the positions of the mechanism shown in FIGS. 13 and 10, sealer 74 and holder 78 move upwardly to their uppermost positions.

Although the invention has been described with respect to particular embodiments thereof, it should be realized that various changes and modifications may be made therein without departing from the spirit and scope of the invention.

What is claimed is:

1. A package enclosing at least one continuous, untangled, flaccid item comprising:
   a fully sealed enclosure including a compartment;
   said flaccid item having an intermediate portion terminating in oppositely disposed end portions, with said intermediate portion being freely housed within said compartment and said oppositely disposed end portions being separately secured to said enclosure; and
   said enclosure having a construction for enabling its rupture and access to said flaccid item portion housed within said compartment for untangled removal therefrom.

2. A package according to claim 1 in which said flaccid item portion housed within said compartment has a randomly bunched-up length which is greater than any internal linear dimension of said compartment.

3. A package according to claim 2 in which said enclosure includes a sealed peripheral portion and a side extending therefrom, and one of said flaccid item end portions is sealed within said sealed peripheral portion and said flaccid item intermediate portion is positioned adjacent said side for enabling at least a segment of said sealed peripheral portion to be separated from said enclosure along a line extending from said side and thereby enabling said segment to act as a handle for the untangled removal of said flaccid item from said compartment.

4. A package according to claim 3 in which said enclosure construction comprises a notch extending partially into said sealed peripheral portion, and said segment comprises a corner of said package.

5. A package according to claim 4 in which said notch comprises a chevron cut pointing in the direction of separation of said segment from said package.

6. A package according to claim 3 in which said enclosure construction comprises a notch extending partially into said side, and said segment comprises at least part of said sealed peripheral portion.

7. A package according to claim 6 in which said notch comprises a chevron cut pointing in the direction of separation of said segment from said package.

8. A package according to claim 2 in which said sealed enclosure comprises a plurality of walls sealed together at their perimeters to define said compartment, with said flaccid item being secured at first and second positions within said sealed perimeter, and with said rupture enabling construction being positioned at least at a first of said positions to permit withdrawal of said flaccid item from said compartment.

9. A package according to claim 8 in which said walls include inner faces of heat-sealable material and outer faces, and said inner faces are heat-sealed at said wall perimeters.

10. A package according to claim 9 in which said outer face of at least one of said walls comprises paper, plastic or aluminum foil.

11. A package according to claim 9 in which said flaccid item comprises a filament of natural fiber, synthetic fiber, metallic wire or combinations thereof.

12. A package according to claim 9 in which said flaccid item comprises dental floss.

13. A package according to claim 1 in which said enclosure construction comprises a package material which is easily torn for providing said segment.

14. A package according to claim 1 in which said enclosure construction comprises at least one tab through which an end of said flaccid item extends, said tab being tearable from said enclosure and acting as said segment.

15. A package according to claim 1 in which said enclosure construction comprises tearing means disposed in the periphery of said compartment for tearing across the compartment to dispense an end of the flaccid item without entanglement.

16. A package according to claim 1 in which said enclosure construction comprises tearing means for tearing across said package to dispense an end of the flaccid item without entanglement.

17. A packaging system for containing segments of a flaccid item comprising a length of tubular material provided with transverse seals at its oppositely disposed ends, and at least one intermediate longitudinal seal extending along the length of said tubular material which divides said tubular material into a plurality of sealed compartments, and at least one continuous, untangled length of said flaccid item in each of said sealed compartments, each flaccid item having an intermediate portion terminating in opposite end portions, with the intermediate portion being freely disposed within said sealed compartment and one of said opposite end portions being disposed within and secured by one of said transverse seals and the other of said opposite end portion being disposed within and secured by the other of said transverse seals.

18. A packaging system according to claim 17 in which each of said longitudinal seals extend sufficiently between adjacent ones of said compartments to enable said tubular material and said flaccid item sealed therewithin to be separated wholly within said seals and to maintain the sealed integrity of said compartment and said flaccid item contained therewithin.

19. A packaging system according to claim 18 in which said flaccid item comprises a filament.

20. A packaging system according to claim 19 in which said filament comprises dental floss.

21. A packaging system according to claim 18 in which said tubular material comprises heat sealable material, and said seals comprise locally heat-sealed portions of said tubular material.

22. A packaging system according to claim 21 in which said tubular material comprises at least two intermediate and parallelly extending longitudinal seals extending generally perpendicular to said transverse seals.

23. A packaging system according to claim 18 in which said tubular material comprises a walled structure having inner and outer surfaces, with heat-sealable material defining said inner surface, and said seals comprise locally heat-sealed portions of said tubular material inner surface.

* * * * *